US005614403A

United States Patent [19]

Ramig et al.

[11] Patent Number: 5,614,403

[45] Date of Patent: Mar. 25, 1997

[54] IN VITRO REPLICATION SYSTEM CAPABLE OF RESCUING CLONED AND MANIPULATED ROTAVIRUS GENES

[75] Inventors: Robert F. Ramig, Houston, Tex.; Dayue Chen, Evanston, Ill.

[73] Assignee: Baylor College of Medicine, Houston, Tex.

[21] Appl. No.: 251,934

[22] Filed: Jun. 1, 1994

[51] Int. Cl.$^6$ .............................. C12N 7/00; C12N 7/01; C12N 7/06; C12P 19/34

[52] U.S. Cl. .................................... 435/235.1; 435/91.21; 435/91.51; 435/238

[58] Field of Search ............................ 435/91.21, 235.1, 435/172.1, 172.3, 91.51

[56] References Cited

PUBLICATIONS

Fujimura et al, The Journal of Biological Chemistry, Jun. 26, 1989, vol. 264(18): pp. 10372–10377.

*Primary Examiner*—David Guzo
*Assistant Examiner*—Terry A. McKelvey
*Attorney, Agent, or Firm*—Fulbright & Jaworski LLP

[57] ABSTRACT

A method for template-dependent in vitro replication and transcapsidation of double stranded RNA from Reoviridae mRNA templates is described. This method provides an efficient means for isolating rotaviral mRNA, manipulating the mRNA, and expressing the new dsRNA species without the use of infected cells by constructing a new virus in the test tube without any cellular components. Viral protein complexes are prepared by test tube degradation of purified virus particles or by expression of a small subset of viral genes in insect cells, where the proteins form complexes. Viral mRNAs are made in the test tube by transcription of "native" viral mRNAs from viral transcriptase particles previously made in vitro, or by expression of viral mRNAs from transcription vectors in vitro. The resultant protein complexes and mRNAs are mixed with a combination of salts and substrates suitable for RNA synthesis, and the enzymatic activity inherent in the protein complexes results in the replication of the mRNA to produce dsRNA. Morphogenesis of the virus particle is completed by sequential transcapsidation with capsid proteins. Thus, the invention provides a method for building viruses with "custom made" genomes, allowing the practitioner to control and manipulate all components of the reaction, since the reaction contains only those components which the practitioner chooses to add. This constitutes the rescue of exogenous genes into rotavirus genomes. Rescue allows the powerful techniques of molecular biology to be applied to the study of viral gene function in the context of the virus-infected cell.

36 Claims, 9 Drawing Sheets

FIG.2A
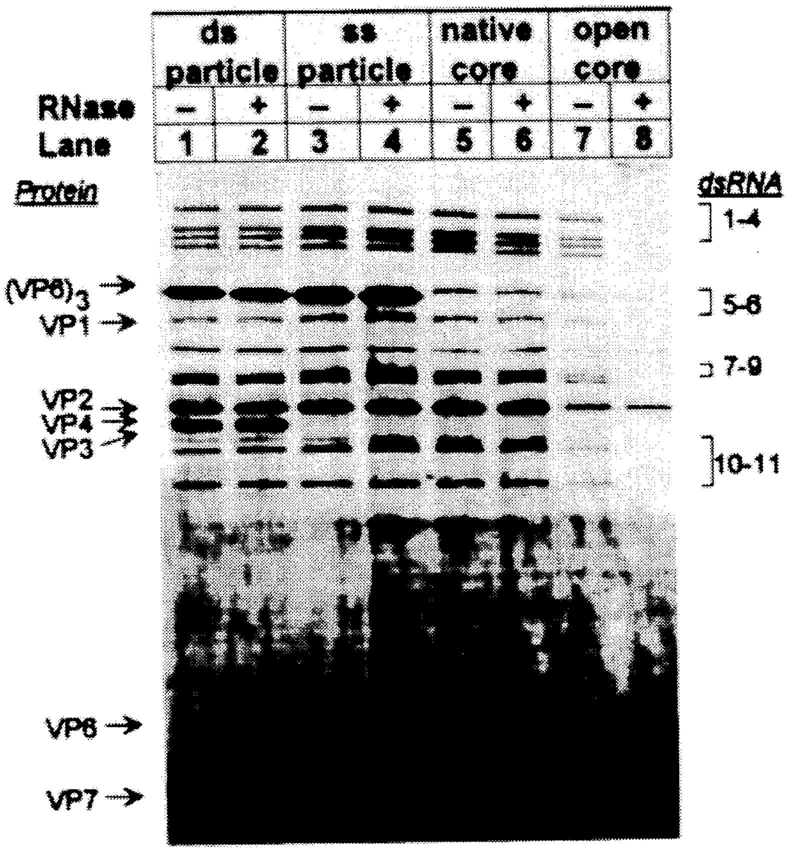
FIG.2B
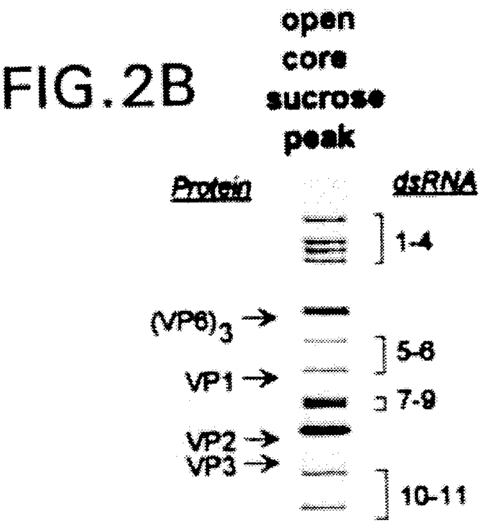
FIG.2C
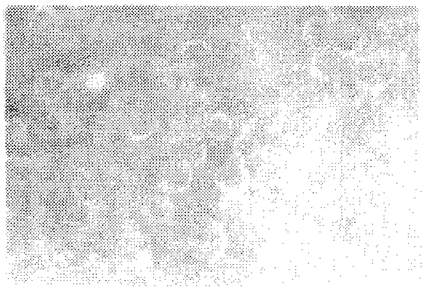
FIG.2D

IN VITRO REPLICATION SYSTEM CAPABLE OF RESCUING CLONED AND MANIPULATED ROTAVIRUS GENES

This invention was supported by a grant from the National Institutes of Health. Accordingly, the U.S. government may have certain rights in this invention.

BACKGROUND OF THE INVENTION

1. Field of the Invention

This invention relates to the use of a template-dependent in vitro system for the replication of double stranded genomic RNA on mRNA templates. This is a major advance that will allow the study and definition of replication signals on the template RNA, and packaging signals in viral packaging complexes and on the packaged mRNA. Second, since this system is template dependent, it allows the manipulation of the input mRNAs so that transcripts made from cDNA clones of double stranded RNA virus genes can be included in the system and replicated. Accordingly, this invention also relates to the rescue of exogenous genes into the genomes of double stranded RNA viruses.

2. Description of the Related Technology

The double stranded RNA (dsRNA) viruses are a large and diverse group, encompassing such dissimilar viruses as [i] the L-A virus of yeast which contains a single chromosome, [ii] the two segmented members of the Birnaviridae, [iii] the lipid-containing bacteriophage $\phi 6$ which has a genome of three segments, and [iv] the members of the Reoviridae (reovirus, rotavirus, orbivirus, etc) which contain a genome of 10–12 segments. More recently, single chromosome dsRNA viruses of parasitic protozoans and the Chestnut blight fungus *Cryhonectria parasitica* have been characterized.

Among the Reoviridae, rotaviruses are documented as the major cause of diarrheal disease in children and the young of mammalian and avian species. In the United States, acute viral gastroenteritis is a common illness affecting all age groups and is second in frequency only to respiratory illness. In the US, the disease is usually self-limiting although it can be lethal in elderly, debilitated, immunocompromised (including AIDS and transplant), or infant patients. In developing areas of the world, diarrhea disease ranks first in both disease incidence and severity, and it has been estimated that in these regions 3–5 billion cases of diarrhea account for 5–10 million diarrhea-associated deaths annually. Rotaviruses are also recognized as significant veterinary pathogens. Thus, the rotaviruses are important human and animal pathogens that cause significant morbidity and mortality.

In the life cycle of rotavirus, the parental genetic material (11 segments of double-stranded RNA) always remains associated with a subviral particle, the transcriptase particle. The genetic information is transmitted to progeny viruses via 11 (+)-sense or messenger RNAs that are single-stranded and are produced by the transcriptase particle from each of the 11 viral genome segments. The mRNA is translated to make viral proteins. Specific viral proteins join with the 11 mRNAs to form complexes called replicase particles. In the replicase particle, the 11 single stranded mRNAs are replicated to form progeny dsRNA genomes with 11 segments of dsRNA. After the dsRNA is formed, non-structural proteins leave the particle and additional viral structural proteins are added to the replicase particle to complete the morphogenesis of the progeny virus particle.

These viruses enter the host cell and replicate in the cytoplasm. After removal of capsid proteins, which activates the virion transcriptase, single-stranded RNA (ssRNA) of messenger or plus (+)-sense is made and expelled from the particle into the cytoplasm (transcription). These ssRNAs can function as message for the synthesis of protein or as template upon which progeny dsRNA genomes are made by synthesis of the complementary negative sense strand. This latter process is traditionally called replication and the enzyme catalyzing (−)-sense RNA synthesis is called the replicase. Relatively little is known about how replication occurs, but studies of replicase complexes isolated from infected cells show that complexes are formed that contain viral structural and nonstructural proteins and a complete set of the (+)-sense template RNAs. After formation of these particulate structures, the replicase is activated and minus (−)-strand synthesis occurs. Perhaps the most unusual feature of this replication pathway is that both transcription and replication occur in particles from which active enzymes have not been solubilized.

Although a great deal has been learned of rotavirus genome structure (the entire genome of 11 segments has been cloned, sequenced and expressed), predicted protein structure, virion structure, antigenic structure and serology, and genetics (FIG. 1), there are still a number of basic questions related to rotavirus biology and molecular biology which remain unanswered, in particular, what are the molecular bases of genome segment assortment and genome replication. With respect to genome segment assortment, researchers are searching for answers to the following questions: What is the mechanism by which genome segments are selected and packaged so that the progeny virions each contain a complete set of genome segments? What are the cis-acting signals on the (+)-strand RNA that direct their binding/packaging by the particulate replicase? What component of the particle binds the binding site on the (+)-strand RNA? What are the packaging requirements for completion of morphogenesis of the subviral particle (SVP) that has segregated a complete set of genome segments? Is the packaging reaction selective for viral (+)-strand RNA, or will it package any ssRNA?

With respect to genome replication, researchers are searching for answers to the following questions: What are the cis-acting signals on the (+)-strand RNA that direct synthesis of the (−)-strand by the replicase? Are there packaging requirements that must be fulfilled for the replicase to be activated? What are the optimum conditions and requirements of the replicase enzyme? If nonviral ssRNAs are packaged, are they replicated? If not, what are the signals for replication of virus-specific (+)-strand RNAs?

The answers to these questions will enhance the understanding of the molecular mechanisms by which complex viruses replicate and interact with the host cell, and will reveal the mechanisms characteristic of rotavirus that will be useful in development of disease control strategies, vaccines and antivirals.

A major stumbling block to finding the answers to these questions and to defining the roles of the various components of the replicase particles has been the absence of a template-dependent in vitro RNA replication system for the Reoviridae. Prior to the present invention, no template-dependent replication system has been described and exploited for the study of RNA replication in any member of the Reoviridae.

Another major stumbling-block to progress in molecular analyses of the Reoviridae is the absence of a system that allows the "rescue" of (+)-strand RNA transcripts of cloned and manipulated cDNAs into infectious virus. A system that could potentially lead to rescue in rotavirus was recently published, reporting replication of exogenously added (+)-strand RNA by replicase particles isolated from rotavirus-infected cells was made (Gorziglia, M. and Collins, P. (1992), Intracellular amplification and expression of a synthetic analog of rotavirus genomic RNA bearing a foreign marker gene. Proc. Natl. Acad. Sci. 89:5784–5788), but this report has not been followed-up. This system is typical of the approach used by many rotavirus labs, without success.

According to this approach, virus-infected tissue culture cells perform the "work" of rescue of an exogenous rotavirus gene (or synthetic gene that looks to the cell like a rotavirus gene) into progeny virus particles. However, the cells used in this approach are not normal cells. These cells have been genetically engineered so that they are expressing a precise copy of a single rotavirus mRNA, even though those cells are not infected. After it is established that the cells are expressing the exogenous rotavirus mRNA, the cells are infected with an ordinary rotavirus using standard conditions for infection. When the infecting rotavirus enters the cell, it produces the 11 rotavirus mRNAs from the transcriptase particle. These 11 "native" rotavirus mRNAs can mix in the cell with the mRNA from the exogenous rotavirus gene. At the stage of the life cycle where viral proteins and mRNAs form replicase particles, it is hoped that by chance the particle will contain 10 of the "native" mRNAs and that the 11th mRNA will the rotavirus mRNA expressed by the cell rather than the equivalent mRNA made by the infecting virus. If this happens, after replication and completion of the life cycle, the progeny virus particle will contain 10 genome segments derived from the infecting virus and the 11th genome segment derived from the exogenous rotavirus gene expressed by the cells. This would constitute rescue of the exogenous gene into infectious virus. The whole process is carried out in the context of the infected cell, and utilizes the normal viral infectious pathways for the life cycle. It is by chance that the extra rotavirus mRNA present in the infected cell becomes incorporated (or rescued) into the progeny virus. There are no reported successes using this system.

The present invention overcomes both of the above-mentioned stumbling blocks and represents a powerful tool for the research of rotavirus and the Reoviridae family of viruses by providing both a system for in vitro replication and a method for the rescue of exogenous genes into infections virus particles.

SUMMARY OF THE INVENTION

It is an object of the present invention to provide a template dependant in vitro replication system for the Reoviridae family of viruses.

It is also an object of the present invention to provide a template dependant in vitro replication system for rotaviruses.

It is another object of the present invention to provide a method for the rescue of exogenous genes into infectious Reoviridae viruses.

It is a further object of the present invention to provide a method for the rescue of exogenous genes into rotavirus genomes.

It is a further object of the present invention to provide a method for the creation of non-naturally occurring double-stranded infectious and non-infectious viruses.

It is a further object of the present invention to provide a method for creating attenuated Reoviridae viruses.

It is a further object of the present invention to provide a kit for the in vitro replication of Reoviridae viruses The problem addressed by the present invention is how to get copies of cloned and genetically manipulated rotavirus genes to enter the replication pathway and become a part of the dsRNA genome of the progeny virus. Being able to do this would allow one to create specific mutations in specific viral genes and use those mutations to study such basic aspects of the virus as replication, transcription, translation and assortment of genome segments, as well as to use the mutations to create attenuated vaccine strains and to study the molecular basis of the host immune response to vaccination.

We have developed a template-dependent, in vitro replication system in which the dsRNA-containing product is indistinguishable from native rotavirus core particles. We have also developed a system in which rotavirus core particles can be transcapsidated sequentially, with inner shell (VP6) protein and outer capsid (VP4 and VP7) protein to yield infectious virus. Together, these systems will provide for the introduction of (+)-strand template RNA transcripts from cloned and manipulated rotavirus genes, their replication and incorporation into core structures, and their rescue following transcapsidation to form infectious virus. Indeed, using this series of in vitro reactions, we can achieve rescue of viral transcripts, including cloned or manipulated rotavirus genes.

The present invention represents an approach to the problem of rescue that is a radically different from the prior art approaches. The in vitro replicase/transcapsidation system of the present invention provides an efficient means for isolating rotaviral mRNA, manipulating the mRNA, and expressing the new dsRNA species without the use of infected cells by constructing a "new" virus in the test tube without any cellular components. This is made possible by a novel mixture containing salts, NTPs and purified VP1, VP2, VP3 rotavirus proteins. The present invention makes use of viral protein complexes, either made [i] by test tube degradation of purified virus particles or [ii] by expression of a small subset of viral genes in insect cells, where the proteins form complexes. The present invention also involves use of viral mRNAs, but these are made in the test tube either by [i] transcription of "native" viral mRNAs from viral transcriptase particles made in vitro, or [ii] by expression of viral mRNAs from transcription vectors in vitro. The protein complexes and the mRNAs are then mixed in the test tube with a suitable combination of salts and substrates for RNA synthesis, and the enzymatic activity inherent in the protein complexes results in the replication of the mRNA to produce dsRNA. Morphogenesis of the virus particle is completed by sequential transcapsidation with inner and outer capsid proteins (See Chen, D & Ramig, RF (1993) Rescue of infectivity by in vitro transcapsidation of rotavirus single-shelled particles. Virology 192: 422–429; Chen, D & Ramig, RF (1993) Rescue of infectivity by sequential in vitro transcapsidation of rotavirus core particles with inner capsid and outer capsid proteins. Virology 194: 743–751) with the result that infectious particles are produced. Both capped native viral mRNAs and uncapped transcripts can be replicated in the system, indicating that the presence of a cap is not required for replication of a template RNA. Furthermore, there does not appear to be a requirement for complete packaging of all 11 templates for activation of replicase activity of the particulate replicase.

In short, the system consists of the following steps:

The rotavirus of interest is grown and purified; the outer and inner capsids are removed.

The mRNA is isolated and manipulated.

The mRNA from the rotaviral species of interest is added to the novel mixture.

The replicase reaction is carried out and results in the replication of the exogenous mRNA.

The inner and outer capsids are replaced.

The end result is a new dsRNA rotavirus containing the genome of the rotaviral species of interest.

The total virus yield is plaque assayed in the presence of antibody in order to find the successfully replicated dsRNA rotavirus if one seeks replacement of neutralizing antigen-encoding genes.

Unlike the approaches that characterize the prior art, the present invention enables one to control the pool of mRNAs from which the selection of mRNA to be incorporated into the particle is made. Thus, a practitioner can remove the element of chance incorporation of the exogenous gene that characterizes the prior art approach. The instant invention accomplishes rescue by building viruses with "custom made" genomes from the most basic components of the virus, the individual viral proteins and the individual viral mRNAs. This process is accomplished in the test tube, and does not involve the use of cells or components derived from cells. This system allows the practitioner to control and manipulate all components of the reaction, since the reaction contains only those components which the practitioner chooses to add. He or she can determine the content of the progeny virus genome; it is not determined by chance.

Accordingly, this invention provides for the first time a method by which a practitioner can isolate a protein complex that has enzymatic activity and which can initiate the synthesis of viral RNA. No one else has been able to establish an in vitro replication system in which rotavirus RNA synthesis is initiated. The present invention affords the practitioner the power to completely define the system. Thus, instead of relying on chance incorporation of an extra (12th) mRNA into a replicase particle, the practitioner can add only eleven mRNAs that are those of his or her choice. Since an infectious virus particle requires one copy of each of the 11 mRNAs replicated to form dsRNA genome segments, if one cloned and manipulated mRNA is added to a pool of the other ten mRNAs from a "native" source, any infectious virus will be required to have rescued the exogenous cloned and manipulated gene.

Prior studies of rotavirus RNA replication in vitro utilized replicase particles isolated from virus-infected cells, and resulted in a description of the RNA and protein composition of the various subviral particles capable of synthesizing dsRNA (Patton (1986) Virus Res. 6:217–233; Patton & Gallegos (1988) Virology 166:358–365; Patton & Gallegos (1990) J. Gen. Virol. 71:1087–1094; Gallegos & Patton (1989) Virology 172:616–627). Cis-acting signals on the template RNAs could not be examined in these studies because the in vitro system was not template-dependent and only allowed run-off synthesis of nascent (−)-strands that had been initiated in vivo. The present invention is a template-dependent, in vitro replication system for replication of rotavirus RNA. The template-dependence of this system, coupled with its ability to utilize in vitro transcripts derived from rotavirus cDNAs, will allow an analysis of cis-acting signals on the RNA templates that are involved in [i] binding of template to the particulate replicase, [ii] packaging of the replication product, and [iii] initiation and synthesis of the (−)-strand RNA. In addition, the discovery that baculovirus-expressed VP1/2/3 particles exhibit replicase activity makes the various components of the particulate replicase accessible to genetic analysis of binding, packaging, and polymerase domains within the individual protein species comprising the particulate replicase.

The instant invention has two unique features that have not been described previously for the Reoviridae family of viruses. First, this system involves the use of a template-dependent in vitro system for the replication of double stranded genomic RNA on mRNA templates. This is a major advance that will allow the study and definition of replication signals on the template RNA, and packaging signals in viral packaging complexes and on the packaged mRNA. Second, since this system is template dependent, it allows the manipulation of the input mRNAs so that transcripts made from cDNA clones of rotavirus genes can be included in the system and replicated. This constitutes the rescue of exogenous genes into rotavirus genomes.

This system has the potential for replication of mRNAs derived from rotavirus cDNAs and their inclusion in core particles that can be transcapsidated to infectious virus. Rescue will allow the powerful techniques of molecular biology (site-directed mutagenesis, etc.) to be applied to the study of viral gene function in the context of the virus-infected cell, rather than by transfection or expression and examination of single viral genes in isolation from the other viral gene products.

The system also provides an improved, more efficient method for creating attenuated viruses and viral vaccines, and affords one the ability to create a vaccine against multiple VP7 (G) and multiple VP4 (P) serotypes versus only two serotype specificities using currently available reassortment technology. The present invention will be a powerful tool for research of rotavirus and other of the Reoviridae, and the development of antiviral strategies and agents. It can also be part of a kit to which the researcher adds the mRNA template from his rotavirus of interest and obtains rotaviral product.

In summary, we have described a template-dependent, in vitro system for the replication of rotavirus dsRNA and a method for rescue of exogenous genes into progeny virus. This system consists of a particulate replicase, (+)-sense RNA templates, and salts and NTPs. Both the template RNAs and the particulate replicase can be derived by in vitro expression of rotavirus cDNAs; expression of templates from transcription vectors and expression of the replicase in cells coinfected with four baculovirus recombinants expressing rotavirus proteins. The ability to express both the templates and the particulate replicase makes both viral components of the system amenable to molecular genetic analyses of signals involved in the replication process. The present invention also represents a powerful tool for the identification of the signals involved in the assortment of rotavirus genes, a process that most likely occurs at the level of recognition of RNA templates during virus assembly. Furthermore, the present invention makes it possible for the first time to transcapsidate particles that have completed the replication of a complete set of rotavirus templates (cores) and rendered them infectious.

BRIEF DESCRIPTION OF THE DRAWINGS

FIG. 2A shows the protein and RNA content of each of the double-shelled (ds), single-shelled (ss), core, and "open" core particles from SA11-4F rotavirus, as well as the RNase susceptibility of the genomic RNA associated with each particle type. The gel was non-reducing, so VP6 runs primarily as trimers, and silver stained, so both proteins and dsRNAs are visible.

FIG. 2B shows concentrated open cores from a sucrose gradient to emphasize the presence of VP1, VP2 and VP3 in the preparation.

FIG. 2C is an electron micrographs of native SA11-4F cores.

FIG. 2D is an electron micrograph of "open" SA11-4F cores.

DESCRIPTION OF THE PREFERRED EMBODIMENTS OF THE INVENTION

The following sets forth a representative example of the template-dependent, in vitro replicase system according to the invention, and its use in the rescue of exogenous genes into infectious virus. The following also describes an example of the utility of the present invention, the use of the instant invention to look into the cis-acting replication signals present on rotavirus mRNA. The instant invention is also capable of achieving rescue of transcripts of cloned and manipulated rotavirus cDNA into infectious virions, as shown in example 15 below. The general strategy reflected in the examples set forth herein is to generate the proteinaceous portions of the reaction (replicase or transcapsidation) from SA11-4F, and to generate the exogenous RNA from the rotavirus B223. SA11-4F and B223 differ in the migration rates for all eleven genome segments (FIG. 1), so that replicase products generated in the assay can be identified as the result of replication of exogenously added RNAs or replication of the background endogenous RNAs present in the protein preparations. SA11-4F was used as the capsid donor because it grows to very high titer and forms capsids that are extremely stable during purification protocols. Nothing in the examples set forth below is intended to limit the invention. The present invention may be practiced equally well with cores and templates derived from any and all rotavirus strains. This will be evident to those of ordinary skill in the art in view of the well known and well documented relatedness between rotavirus strains. The present invention may also be practiced with cores and templates derived from other members of the Reoviridae family.

Figure 1:
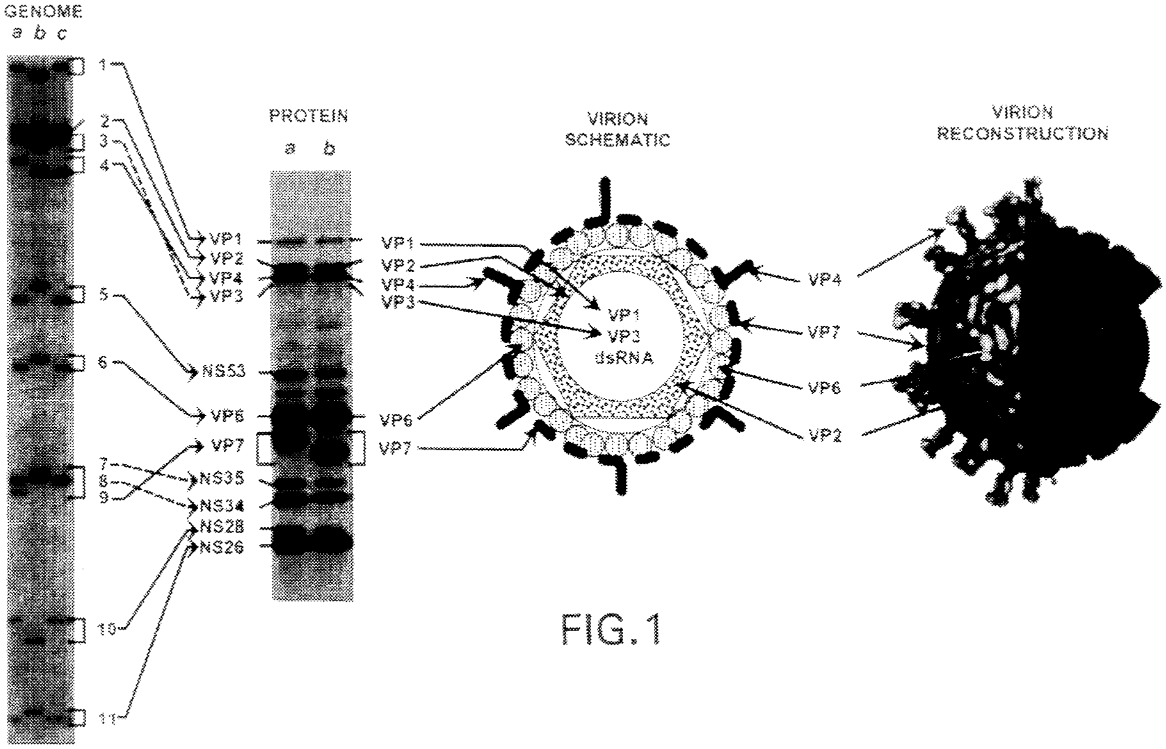
FIG. 1 shows the coding assignments and virion locations of rotavirus proteins and the three dimensional structure of the rotavirus particle. Genome: shows electrophoretic profile of 3 virus strains (a=SA11-CI4; b=B223; c=SA114F). Protein: shows rotavirus proteins and segments in which they are encoded. Virion Schematic: shows locations of proteins in the three layers of the rotavirus capsid. Virion Reconstruction: shows surface representation of the three dimensional structure of the three rotavirus capsid layers. The protein species comprising the surface of each capsid layer is indicated.

Note on nomenclature: Rotavirus has classically been called a double capsid virus, although recent studies have shown it contains three capsid layers (FIG. 1, Reconstruction). In an attempt to retain consistency with the classical terminology we will use the following nomenclature: Double-shelled (ds) particles are complete virions that have all three capsid layers and display VP4 and VP7 on their surface. Single-shelled (ss) particles lack the outer layer of VP4/VP7, display VP6 on their surface, and have transcriptase activity. Core particles lack the two outer capsid layers (VP4/VP7 and VP6) and display VP2 on their surface. Open core particles are core particles that have been dialyzed against low ionic strength buffer and have replicase activity.

Cells and Viruses

EXAMPLE 1

MA104 monkey kidney cells were grown in Medium 199 containing 5% fetal bovine serum and used for rotavirus propagation as described (Ramig (1982) Virology 120:93–105). *Spodoptera frugiperda* (Sf9) insect cells were grown in Grace's medium and used for propagation of recombinant baculoviruses as previously described (Estes et al (1987) J. Virol. 61:1488–1494).

EXAMPLE 2

Rotavirus strains SA11-4F and B223 were from the laboratory collection and have been described previously (Burns et al (1989) Virology 169:427–435; Chen et al (1989) Proc. Natl. Acad. Sci. USA 86:3743–3747). Recombinant baculovirus strains expressing the following rotavirus protein species were used: VP1, pVL941/Rf1 (Cohen et al (1989) Virology 171:131–140); VP2, pVLRF2A (Labbe et al (1991) J. Virol. 65:2946–2952); VP3, pVL1393/SA11-3 (Liu et al (1992) Virology 188:77–84); and VP6, pAC461/SA11-6 (Estes et al (1987) J. Virol. 61:1488–1494).

Preparation of Rotavirus Particles with Replicase Activity

EXAMPLE 3

"Open cores" from native virions: Core particles of native SA11-4F, devoid of dsRNA (or in which the dsRNA was nuclease accessible, so that the particles are called "open") were prepared as follows (Chen & Ramig (1993) Virology 194:743–751): [i] Complete double-shelled virus was purified from infected MA104 cells by a standard freon extraction-pelleting-CsCl procedure (Chen & Ramig (1992) Virology 186:228–237). [ii] The outer capsid (VP4 and VP7) was removed by suspending purified virus in tris-buffered saline (pH 7.8) containing 50 mM disodium EDTA and incubating for 30 minutes at 37° C. The resulting single shelled particles were separated from the VP4 and VP7 in the supernatant by centrifugation. [iii] Core particles were produced by suspending single shelled particles in TBS containing 1.0M $CaCl_2$ and incubating for 20 minutes at 37° C. Core particles were purified by CsCl centrifugation and dialysis into TBS. [iv] To remove the dsRNA from the native core particles, the particles were dialyzed 18 hours at 4° C. against 2 mM Tris-HCl, pH 7.6, containing 0.5 mM disodium EDTA and 0.5 mM dithiothreitol. After dialysis, the resulting "open core preparation was stored at 4° C. until use (preparations of open cores for up to 45 days with no apparent loss of activity). "Open" cores were sometimes further purified by CsCl gradient centrifugation prior to dialysis into the low ionic strength buffer and storage in the presence of 0.01% $NaN_3$.

FIG. 2A shows the protein and RNA content of each of the particle types generated, as well as the RNase susceptibility of the genomic RNA associated with each particle type at each step leading to the production of open cores. Double-shelled particles contained the normal complement of proteins (lane 1) and the dsRNA was RNase resistant (lane 2). Removal of the outer capsid by EDTA treatment produced normal single-shelled particles in which the dsRNA was RNase resistant (lanes 3, 4). Treatment with 1M $CaCl_2$ removed VP6 and produced core particles in which the dsRNA was RNase resistant (lanes 5, 6). Preparations of open cores contain the proteins VP1, VP2 and VP3, and the dsRNAs. Dialysis of the core particles against low ionic strength buffer for 18 hr produced "open core particles" in which the dsRNA was RNase susceptible (lanes 7,8). It is unclear if the dsRNA of the open cores exits the particle or if the dsRNA is made accessible to RNase by treatment of the cores with low ionic strength buffer. That is, the sensitivity to RNase A of the sdRNAs in the open cores suggests that the dsRNAs have either leaked out of the cores structure or that the core structure is open enough to allow penetration of the nuclease. Electron micrographs of native cores (FIG. 2C) and open cores (FIG. 2D) suggest that the open core particles are empty. The proteins of open core particles are subject to digestion with trypsin, whereas those of ds-, ss- and core particles are not (data not shown). When the open cores are used for replicase reactions, they prefer to replicate exogenously provided (+)-strand RNA to the endogenous dsRNA in the preparation (see below).

EXAMPLE 4

Baculovirus-expressed virus-like particles: The baculovirus-expressed equivalent of "open core" particles (bac-cores) were produced by the coexpression of VP1/2/3/6 in insect cells as follows. Sf9 insect cells were coinfected with a multiplicity of infection of 5 PFU/cell each with baculovirus recombinants pVL941/Rf1, pVLRF2A, pVL1393/SA11-3, and pAC461/SA11-6. After two hours adsorption, the infected cells were pelleted and resuspended in Grace's medium containing 0.5% fetal bovine serum and incubated at 27° C. Six to seven days postinfection, the cells were pelleted from the medium and the supernatant was pelleted through a cushion of 35% sucrose by centrifugation for 90 min at 25,000 RPM in a SW28 rotor. The pellet was resuspended and subjected to isopycnic CsCl gradient centrifugation for 18 hr at 35,000 RPM in a SW 50.1 rotor. The visible band was collected by side puncture of the centrifuge tube and dialyzed against Tris-buffered saline. The resulting VP1/2/3/6 particles were converted to open cores as follows. The VP6 was removed by dialysis overnight against 1.0M $CaCl_2$ at 37° C. The resulting VP1/2/3 particles were "opened" by dialysis of the core particles into low ionic strength buffer (2 mM Tris-HCl, pH 7.6, 0.5 mM EDTA, 0.5 mM DTT) for 18 hours. The "open" VP1/2/3 particles were stored in the presence of 0.01% $NaN_3$.

Figure 3A:
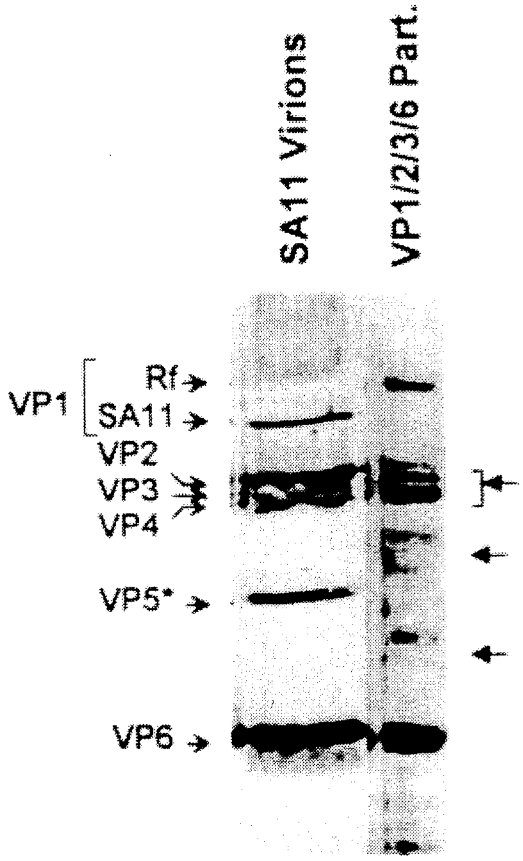
FIG. 3A shows the content of native SA11-4F virions as compared to baculovirus-expressed VP1/2/3/6 particles.
Figure 3B:
FIG. 3B shows an electron micrograph of baculovirus-expressed VP1/2/3/6 particles.

Four rotavirus proteins were coexpressed as we found that expressed particles containing VP1/2/3 aggregated strongly during purification (data not shown) whereas particles containing VP1/2/3/6 (bac-ss-particles; FIG. 3A) could be obtained as a monodisperse suspension (FIG. 3B). Expressed bac-ss-particles contained VP1/2/3/6, although much of the VP2 was present in the form of degradation products (FIG. 3A). The expressed bac-ss-particles were purified and converted to core particles and then to open cores as for native ss-particles. The baculovirus-expressed particles appeared to contain no RNA (FIG. 3B), and no endogenous RNA could be detected in gels (data not shown). The resulting "open" bac-cores have replicase activity (see below).

Preparation and Characterization of RNA Templates

EXAMPLE 5

Native mRNA templates: Messenger RNA was produced from virus strain B223 using the endogenous transcriptase of the ss-particle as follows. B223 single-shelled particles were prepared as previously described (Chen & Ramig (1993) Virology 192:422–429). Positive-strand, template RNA (mRNA) to program the replicase reaction was prepared from rotavirus strain B223 single-shelled particles using a standard in vitro transcription protocol (Mason et al (1980) J. Virol. 33:1111–1121), modified by substituting the RNase inhibitor RNAs in (200 U/ml) for bentonite. After the transcription reaction was run, the mRNA products were treated as follows: [i] The single-shelled particles were removed by centrifugation (SW50.1, 45 k rpm, 1 hr, 4° C.). [ii] The reaction was adjusted to 1% SDS and extracted twice with water-saturated phenol. [iii] The aqueous phase from phenol extraction was precipitated with ethanol. [iv] The precipitated RNA was dissolved and adjusted to 2M $LiCl_2$ to precipitate the mRNA away from any dsRNA from broken ss-particles. [iv] The (+)-strand (m)RNA was dissolved and precipitated with ethanol. [v] The (+)-strand (m)RNA was collected, dissolved in $H_2O$, and aliquots were stored at −70° C. until use. In some reactions, the (+)-strand (m)RNA was labeled with $^{32}P$ by including α-[$^{32}P$]-UTP, or labelled with $^3H$ by including [5,6-$^3H$]-UTP, in the transcription reaction. Analysis of radiolabelled (+)-strand (m)RNA preparations by electrophoresis and autoradiography showed no detectable dsRNA. The resulting mRNAs were tested for integrity by confirming the presence of all 11 full-length mRNAs in gels and in vitro translation, where they directed the synthesis of all 11 rotavirus protein species (data not shown).

EXAMPLE 6

Figure 4:
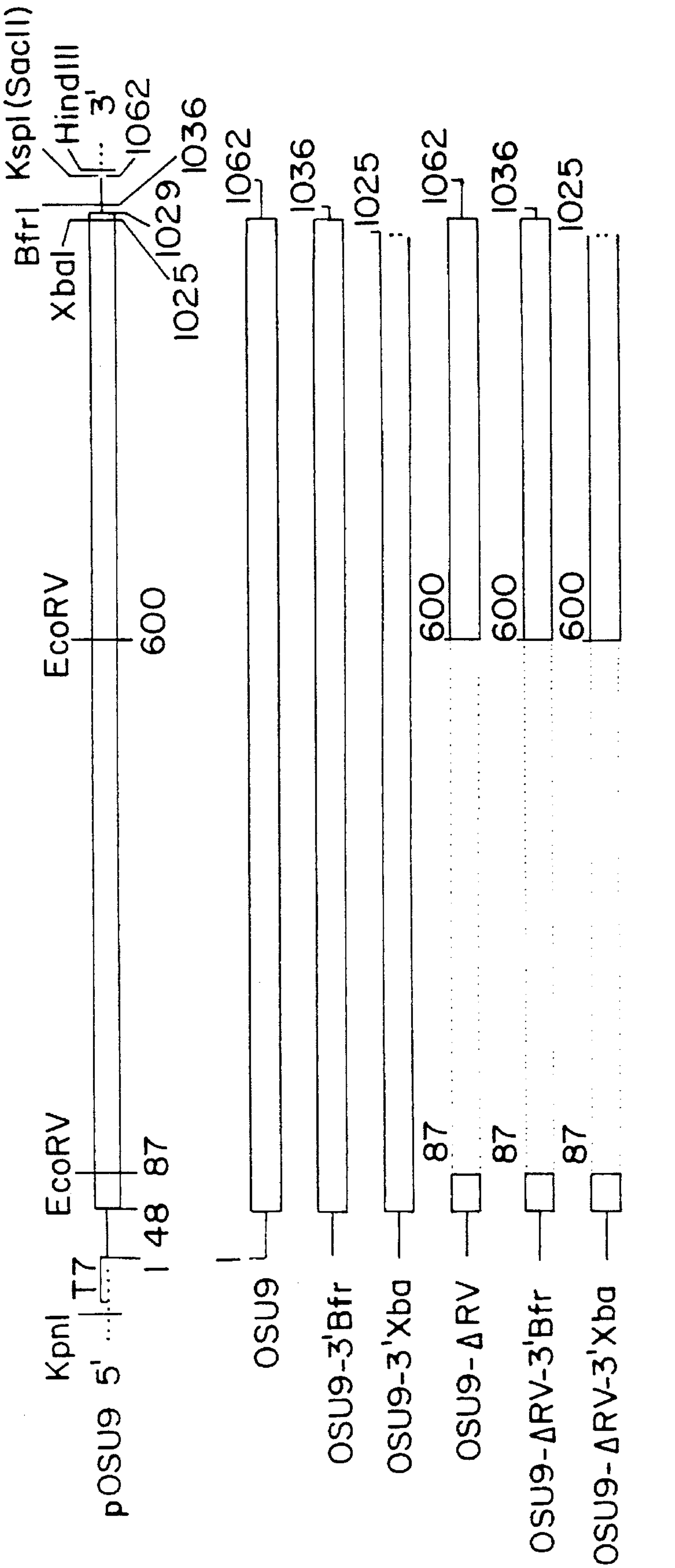
FIG. 4 shows the structures of various reporter RNA templates.

Reporter RNA templates: A cDNA clone of rotavirus strain OSU genome segment 9, under the control of the T7 promoter and having precise 5'- and 3'-termini, was generated by PCR and cloned into pUC19 as described in examples 7 and 8 below. Linearization of the resulting plasmid (pOSU9) with KspI (SacII) and transcription with T7 polymerase yielded a transcript with precise 5'-GG . . . and CC-3' termini. An internal deletion was constructed by deletion of the EcoRV fragment extending from nt 87-600 (pOSU9-DRV). Two 3'-terminal truncations were generated by linearizing pOSU9 with BfrI (26 nt short) or XbaI (37 nt short). In addition, the internal deletion was combined with the terminal truncations. The structures of the resulting reporter RNA templates are shown in FIG. 4.

Figure 5:
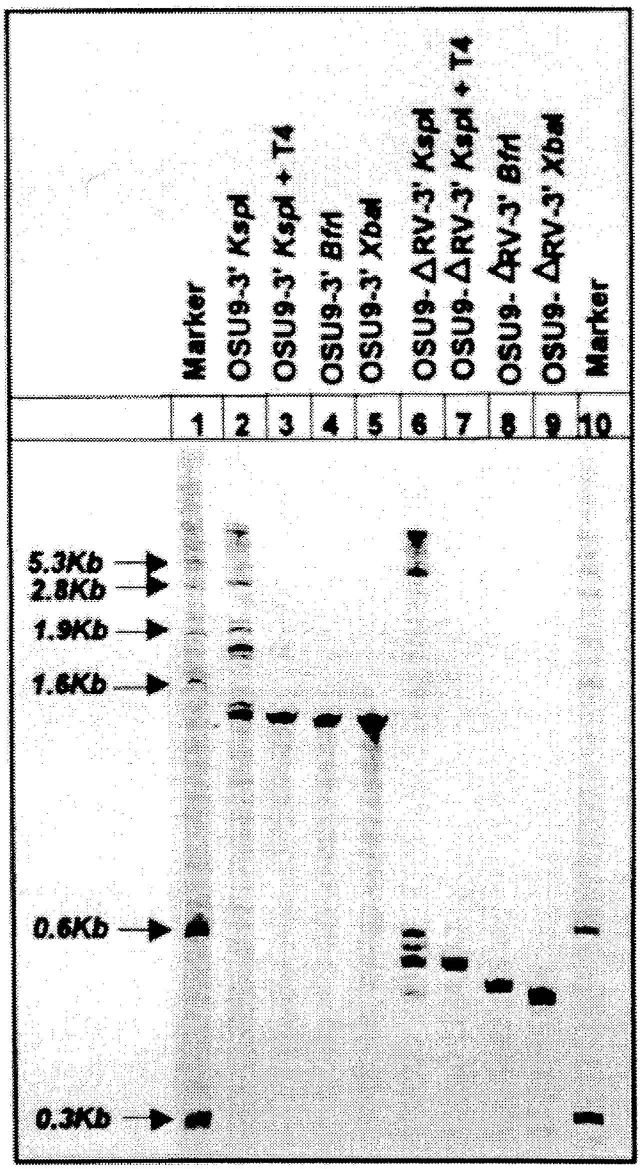
FIG. 5 shows the relative sizes of the various reporter RNA templates

Analysis of the transcripts resulting from these constructs (FIG. 5) showed that linearization of pOSU9 with KspI produced transcripts predominantly the expected 1062 nt in length but, in addition, longer transcripts were produced (lane 2). Filling in the 3'-overhang of the KspI-cut pOSU9 with T4 DNA polymerase prior to transcription resulted in synthesis of only the expected 1062 nt transcript (lane 3). Similar results were observed with pOSU9-DRV (lanes 6,7). Transcription of the plasmids truncated with BfrI (lanes 4, 8) or XbaI (lanes 5,9) resulted in the expected size transcripts.

EXAMPLE 7

Construction of the rotavirus strain OSU segment 9 transcription vectors: A transcription vector for the expression of full-length OSU segment 9 transcripts with precise, native 5'- and 3'-termini was constructed. A PCR-modified cDNA of OSU segment 9 (GenBank accession number x04613) under the control of the T7 promoter was generated by reverse transcription-PCR using the following primers. [i] The positive sense primer was:

5'- CCAGGTACCT AATACGACTC ACTATAGGCT TTAAAAGAGA GAATTTCCG ACTGG -3'(SEQ. ID NO.: 1)

where the T7 promoter is double underlined, the Kpnl site for cloning is single underlined, and the viral sequence is italicized. [ii] The negative sense primer was:

5'- GGTAAGCTTC CGCGGTCACA TCATACAGTT CTAAC-3'(SEQ. ID NO: 2)

where the SacII (KspI) site for cleavage to yield a precise 3'-end on the transcript is double underlined, the HindIII site for cloning is single underlined, and the viral sequence is italicized. The PCR-modified OSU segment 9 cDNA was then cloned into the KpnI/HindIII site of pUC19 to yield pUC/OSU9. Clones containing the desired insert were confirmed by restriction digestion and sequencing of ~250 nt across each cloning boundary using pUC19 sequencing primers.

An internal deletion construct was derived by a one-step subcloning procedure using the two EcoRV sites in the OSU9 insert to remove nt 90 to 602 of the OSU9 sequence. pUC/OSU9 was cut with EcoRV and the plasmid blunt-end ligated to produce pUC/OSU9-ΔRV.

EXAMPLE 8

Transcription of OSU segment 9 cDNAs: Plasmids pUC/OSU9 and pUC/OSU9-ΔRV were linearized with SacII, BfrI, or XbaI so that various length transcripts would be obtained. The 3'-terminal overhang of SacII linearized DNA was blunt-ended in some cases using T4 DNA polymerase at room temperature for 20 min. The linearized plasmids were then transcribed using T7 RNA polymerase (Promega) as recommended by the manufacturer. Following transcription reactions, the DNA templates were removed by RQ1 RNase-free DNase (Promega) at 37° C. for 15 min., and the transcripts were recovered by ethanol precipitation.

in vitro Replication of Rotavirus RNA

EXAMPLE 9

An in vitro system was constituted and programmed with "open cores" derived from SA11-4F and template mRNAs derived from B223 as follows. The initial replicase reactions that successfully synthesized dsRNA on exogenously added (+)-strand template RNA consisted of 30 μl and contained the components and concentrations shown in Table 1:50 mM Tris-HCl (pH 7.8), 10 mM Mg-acetate, 1.25 mM of ATP, GTP, and CTP, 0.5 mM UTP, 8 mM Phosphoenolpyruvate, 50 μg/ml pyruvate kinase, 1mM S-adenosyl-L-methionine, 2 mM dithiothreitol (DTT), 800 U/ml RNAsin, 15 μCi α-[$^{32}$P]-UTP (3000 Ci/mM), 0.4 μg total B223 transcripts, and 0.3 μg SA11-4F "open" cores. The concentration of open cores was determined by the BioRad protein assay; that of (+)-strand RNA by O.D. The reaction was carried out at 37° C. for 120 minutes, and the products were analyzed on 12% SDS-polyacrylamide gels.

TABLE 1

Composition of the Initial and Optimized Replicase Reactions

| Reaction Component | Initial Reaction | Optimal Reaction |
|---|---|---|
| Tris-HCl | 50 mM, pH 7.8 | 100 mM, pH 7.2 |
| Magnesium Acetate | 10 mM | 5 mM |
| ATP, GTP, CTP (each) | 1.25 mM | .1 mM |
| UTP | 0.5 mM | 0.04 mM |
| Dithiothreitol | 2 mM | 2 mM |
| RNasin | 800 U/ml | 800 U/ml |
| "Open Cores" | 200 ng | 800 ng |
| Template RNA | 3600 ng | 1000 ng |
| α-[$^{32}$P]-UTP | 15 μCi | 10 μCi |
| Phosphoenol Pyruvate | 8 mM | — |
| Phosphoenol Pyruvate Kinase | 50 μg/ml | — |
| S-Adenosyl Methionine | 1 mM | — |
| Polyethylene Glycol 4000 | — | 1.5% |
| Total Reaction Volume | 30 μl | 20 μl |
| Reaction Time | 120 min | 180 min |
| Reaction Temperature | 37° C. | 35° C. |

Figure 7:
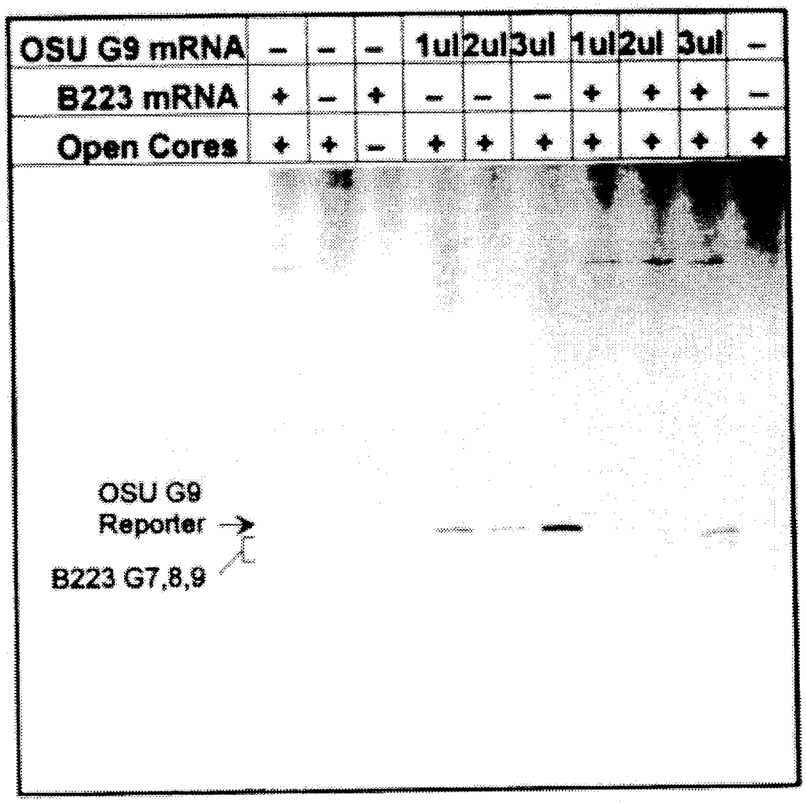
FIG. 7 shows the results of in vitro replication using OSU G9 mRNA templates or B223 mRNA templates with SA11-4F "open cores."
Figure 8:
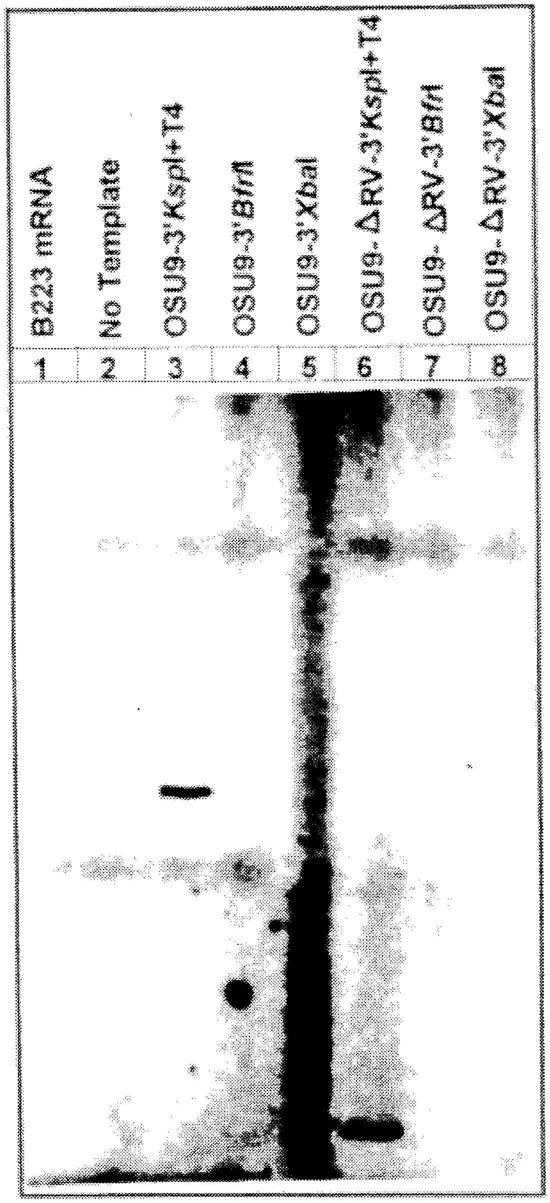
FIG. 8 shows the results of in vitro replication using various synthetic reporter templates and SA11-4F "open cores."

More specifically, FIG. 8 shows that when the products of this reaction were labelled by inclusion of α-[$^{32}$P]-UTP (FIG. 6) labelled products were obtained that had gel mobility of B223 dsRNA (lane 1) and were RNAse resistant (lane 2). Under these conditions, the various dsRNA species were produced in non-equimolar amounts, with segments 5, 6, 10, and 11 being underrepresented. Segment 10 was most underrepresented and is not visible in FIG. 7, but is visible in longer exposures of the gel. If exogenous mRNA was omitted from the reaction (lanes 3 & 4), smaller amounts of dsRNA having the gel mobility characteristics of SA11-4F dsRNA were synthesized. This dsRNA was presumably made using the (+)-strand of the remaining endogenous dsRNA present in the "open core" preparation as template. The synthesis of dsRNA from the endogenous RNA appears to be suppressed if exogenous RNA templates are provided to the system (lanes 1, 2). If no "open cores" (lanes 5, 6) or native cores (lanes 7, 8) were added to the reaction, no dsRNA products were synthesized, showing the requirement for "open" cores as a source of the replicase enzyme responsible for the dsRNA product. Quantitatively similar results were obtained if the label was supplied to the reaction in the form of α-[$^{32}$P]-CTP or [5,6-$^{3}$H]-UTP (data not shown). If the label was supplied to the reaction in the form of α-[$^{32}$P]-UTP-labelled B223 mRNAs, the reaction products were labeled demonstrating that the mRNA was actually serving as template in the reaction (data not shown).

Optimization of the in vitro Replication System

EXAMPLE 10

While our initial in vitro replication system synthesized dsRNA on mRNA templates (FIG. 6), the incorporation was somewhat low and gel exposures took on the order of 2–7 days.

We carried out a thorough optimization of the in vitro replication reaction using SA11-4F-derived "open cores" as the particulate replicase and in vitro synthesized OSU segment 9 transcripts as the template. The requirement for, and optimal concentrations of, the various components of the replication system were systematically examined using "open" cores from SA11-4F as the source of replicase and transcripts from pUC/OSU9 as the reporter template. The kinetics of the reaction were examined by analyzing aliquots taken from a mass reaction at various times of incubation.

The results of this optimization are summarized in Table 1, which compares our initial system to the optimized system. Direct comparison showed that the optimized system incorporated greater than 10-fold more counts into dsRNA as compared to the initial system. Using the optimized system, strong autoradiographic bands could be detected in 12–18 hour exposures.

Several points relative to optimization merit comment: [i] Phosphoenol pyruvate, phosphoenol pyruvate kinase, and S-adenosyl-methionine were not required for activity and their omission reduced the background of RNase resistant material synthesized. [ii] We examined the requirement of the replicase reaction for divalent cations. We found that the optimal replicase reaction required either Mg++ at 2.5–5.0 mM, or Mn++ at 2.5 mM, but maximal incorporation was obtained with Mg++ at 5 mM. [iii] The replicase activity was optimal at pH 6.5. Incorporation into dsRNA fell off slowly above pH 6.5 and activity was not detectable at pH 8.5. We chose, in our optimal system, to use pH 7.2 to stay within the buffering range of Tris-HCl. [iv] The replicase activity functioned over a wide temperature range with the optimum being 33°–35° C. [v] The replicase activity was optimal at relatively low salt concentration. Addition of either Na+ or K+, as either chloride or acetate salts, inhibited the reaction at concentrations as low as 25 mM. [vi] Polyethylene glycol was not absolutely required for replicase activity, but addition of PEG-4000 at concentrations up to 1.5% significantly stimulated incorporation. [vii] Kinetic studies showed that in vitro replication products could be detected in as little as 10 minutes of reaction, and the product continued to accumulate until approximately 4 hours of reaction. The optimal time of reaction was determined by running a mass reaction consisting of the basic reaction, and removing aliquots at various times for analysis of the products by PAGE. Complete dsRNA products were first detectable at 20–30 minutes of reaction at 37° C., and increased in intensity until 150–180 minutes of reaction. By 180 minutes the accumulation of dsRNA product appeared to plateau. The reaction is now standardly incubated for 180 minutes. [viii] The strength of the autoradiographic signal could be increased by reducing the concentrations of the NTPs to raise the specific activity of the $\alpha^{32}$P-UTP used as label. The optimal concentrations were 0.1 mM for ATP, GTP, and CTP, and 0.04 mM for UTP. [ix] DTT is required for the activity of the RNasin in the system to protect the template RNA from degradation. DTT did not inhibit the reaction at concentrations below 10 mM, and 2 mM is used. [x] The ratio of particulate replicase enzyme to mRNA template was examined and found to be 0.8 ug open cores to 1.0 ug template RNA. [xi] Finally, it is clear that the product of the reaction is dsRNA. The product is resistant to digestion with RNase A in high salt conditions, but if the salt concentration is dropped below about 0.10M, the product is completely digested. This is classic nuclease susceptibility of dsRNA.

Replication of Reporter Template RNAs

EXAMPLE 11

To determine if the in vitro replicase would replicate synthetic rotavirus RNA templates, we programmed the system with SA11-4F "open cores" and various exogenous template RNAs as shown in FIG. 7. When the system was programmed with B223 mRNAs the standard B223 dsRNAs were made (lane 1). If no exogenous RNA was added to the system (the control reaction), a very weak background level of SA11-4F dsRNA was made (lane 2). No dsRNA was synthesized in the absence of open cores (lane 3). Programming the system with increasing amounts of transcript derived from KspI-linearized pOSU9, resulted in the synthesis of increasing amounts of dsRNA with the mobility of OSU segment 9 (lanes 4–6). Adding increasing amounts of OSU9 transcript with a constant amount of B223 mRNA resulted in both B223 and OSU segment 9 dsRNAs being synthesized, with the relative amount of OSU segment 9 increasing in parallel with the input of OSU9 transcript (lanes 7–9). If the reaction contained the linearized pOSU9 plasmid from which the OSU9 transcripts were derived, no dsRNA product was made (lane 10). These results indicated that a mRNA, derived from a cloned gene and having precise 5' and 3'-termini, could be replicated in the system.

We obtained a PCR-amplified genome segment 9 (encodes VP7) of porcine rotavirus strain OSU from Dr. Mario Gorziglia (LID-NIAID). The PCR product had two important properties: [i] The 5'-terminal primer added a T7 promoter so that transcription began precisely at the same nucleotide as the native mRNA. [ii] The 3'-terminal primer introduced a SacII site such that run-off transcription to the SacII site produced the same 3'-terminal nucleotide as in the above mRNA. We cloned this PCR product into pUC19, and sequenced about 250 nucleotides from each end of the insert to verify it contained authentic segment 9 termini. Transcripts were produced from the plasmid, which had been cut with SacII, using T7 polymerase.

Cis-acting Replication Signals on Template RNA

EXAMPLE 12

The in vitro replication system according to the invention was used to investigate the locations of cis-acting replication signals on a template RNA representing segment 9 of virus strain OSU. Possible locations of replication signals on the template RNAs were examined by programming the in vitro replication system with transcripts of an internal deletion (OSU9-ΔRV) or 3'-terminal truncated transcripts derived from either the full-length OSU9 plasmid or the deletion plasmid (FIG. 4). The replication system with SA11-4F-derived open cores synthesized B223 dsRNAs when programmed with B223 mRNA (FIG. 8, lane 1), and very slight amounts of SA11 4F dsRNA when no exogenous template was added (lane 2). Full-length OSU9 transcripts, derived from KspI-linearized pOSU9, programmed the synthesis of OSU genome segment 9 (lane 3). OSU9 transcripts truncated by 26 3'-nt by linearization of the transcription plasmid at the BfrI site were not detectably replicated (lane 4). Similar results were found for transcripts truncated by 33 3'-nt by linearization of the plasmid at the XbaI site (lane 5). An internal deletion of OSU9, produced by transcription of pOSU9-ΔRV linearized with KspI, was replicated and resulted in a dsRNA 513 bp shorter than that produced from the parental OSU9 transcript (lane 6). The requirement for the 3'-terminal 26 and 33 nt was confirmed by truncation of OSU9-ΔRV transcripts at the BfrI or XbaI sites, respectively. Neither of the truncated deletion transcripts was replicated (lanes 7, 8).

These results, specifically, the ability of OSU9-ΔRV transcripts to be replicated, indicate that no required replication signals reside within the EcoRV fragment extending from nucleotides 87–600 of the 1062 nt OSU segment 9. Furthermore, the failure of transcripts with 3'-terminal truncations of 26 and 33 nt indicate that cis-acting replication signals reside very near the 3'-terminus of the OSU9 template. We also have constructed a deletion mutant of the reporter (548 nt long) in which 514 of the 1062 nucleotides (from 90 to 602) were deleted. The deleted reporter is also replicated in the system, indicating that signals important for replication do not reside in the region from 90 to 602 nt (data not shown). Any signal residing at the 5'-terminus must lie within the first 87 nt to be consistent with the replication of OSU9-ΔRV.

Template Specificity of the in vitro Replication Reaction

EXAMPLE 13

The ability of non-rotavirus RNAs to serve as template was examined. A number of natural and synthetic single-stranded RNAs were obtained, and tested for their ability to direct the synthesis of the relevant protein, prior to being used to program the in vitro replication system. Template specificity was determined by programming the optimized reaction with the following non-rotavirus RNAs: luciferase mRNA, brome mosaic virus RNAs, tobacco ring spot virus RNAs, and T7 transcripts of Norwalk virus RNA. Specificity was examined in the presence of either Mg++ or Mn++.

None of the following RNAs was replicated in the in vitro replication system: luciferase mRNA, tobacco ring spot virus RNAs, brome mosaic virus RNAs, and T7 transcripts of Norwalk virus RNA (data not shown). The failure of non-rotavirus RNAs to be replicated suggested specific recognition of rotavirus templates by the particulate replicase.

Baculovirus-Expressed Virus-Like Particles Have Replicase Activity

EXAMPLE 14

Figure 6:
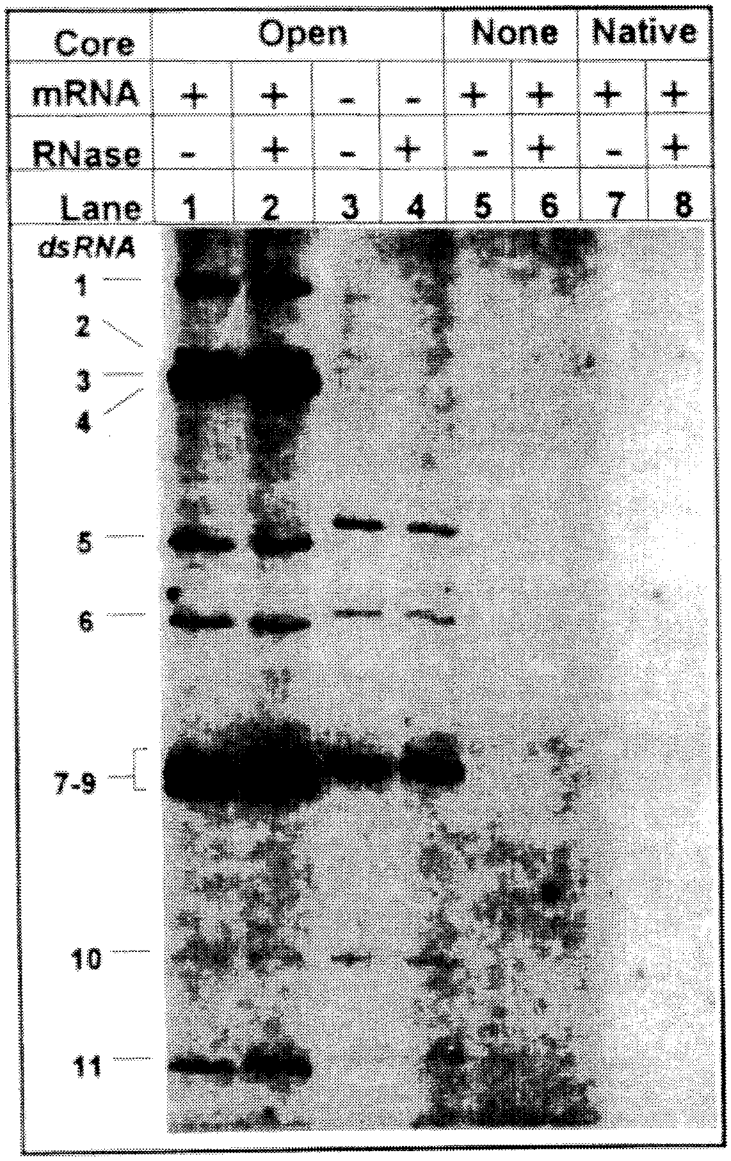
FIG. 6 shows the results of in vitro replication using B223 derived template mRNAs and SA11-4F derived "open cores."
Figure 9:
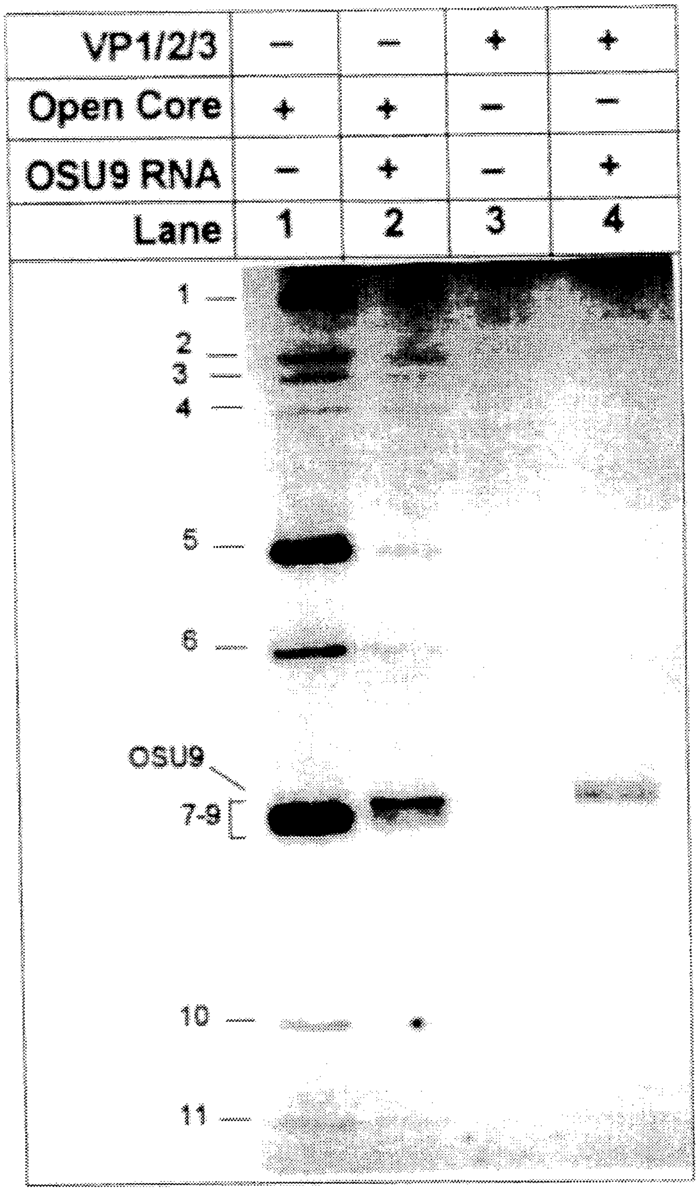
FIG. 9 show the results of in vitro replication using OSU9 mRNA template with Baculovirus-expressed VP1/2/3 particles (bac-cores) and with SA11-4F derived "open cores."

Baculovirus-expressed VP1/2/3 particles (FIG. 3) were prepared and tested in the optimized in vitro replicase assay for replicase activity. Coinfection of insect cells with combinations of baculovirus vectors expressing individual genome segments has resulted in coexpression and assembly of the rotavirus proteins into virus-like particles (VLPs). One of the VLPs contains VP1/2/3, the same protein composition as the open cores prepared from virions. These VLPs aggregated and could not be purified as a monomeric suspension. However, VLPs containing VP1/2/3/6 could be purified and did not significantly aggregate. Accordingly, VP1/2/3/6 VLPs were purified and then treated sequentially with chaotropic agent (1M $CaCl_2$) followed by dialysis against low ionic strength buffer (2 mM Tris-HCl, pH7.6, 0.5 mM EDTA, 0.4 mM DTT). This treatment yielded reasonably well-dispersed "open" VP1/2/3 particles, which were then tested for replicase activity in the standard assay, using the OSU9 reporter RNA as the exogenous template (FIG. 9). The SA11-4F-derived open core control (lane 1) synthesized significant amounts of dsRNA from the endogenous SA 11-4F RNAs present in the preparation. When SA11-4F-derived open cores were programmed with OSU9 template (lane 2) the amount of dsRNA from endogenous template was significantly reduced and large amounts of dsRNA were made from the OSU9 template. Open VP1/2/3 VLPs ("Bac-cores") made no dsRNA if no exogenous template was provided (lane 3). If open VP1/2/3 VLPs were programmed with OSU9 template, OSU segment 9 dsRNA was made on that template (lane 4). In other experiments, the in vitro replication reaction programmed with bac-cores and B223 mRNAs produced B223 dsRNAs (data not shown), although the molar ratios of the various dsRNA species were unequal like those produced by open cores (FIG. 6, lane 1). These results show for the first time that: [i] baculovirus-expressed VLPs of appropriate protein composition can exhibit replicase activity; [ii] replication can occur in the absence of nonstructural proteins, since Bac-VLPs come from cells completely devoid of rotavirus nonstructural protein, and [iii] because Bac-VLPs contain no RNA, replicase particles derived from them produce no background resulting from replication of endogenous RNA. Taken together, these results show further that a functional in vitro replication system for rotaviruses can be reconstituted from [i] a baculovirus-expressed particulate replicase, [ii] in vitro synthesized transcripts of rotavirus cDNAs, and [iii] a simple combination of salts and NTPs. Thus, both the particulate replicase and the template RNAs are subject to genetic manipulation.

Application of the Replicase System to Rescue of Exogenous Rotavirus Genes

EXAMPLE 15

We recently showed that we can obtain infectious virus by sequential transcapsidation of native rotavirus cores, first with VP6 to make a single-shelled particles followed by VP4 and VP7 to make a double-shelled particles (Chen, D & Ramig, RF (1993) Rescue of infectivity by in vitro transcapsidation of rotavirus single-shelled particles. Virology 192: 422–429; Chen, D & Ramig, RF (1993) Rescue of infectivity by sequential in vitro transcapsidation of rotavirus core particles with inner capsid and outer capsid proteins. Virology 194: 743–751). In these studies native cores were prepared as described above, as was VP6 and the VP4/VP7 mixture. Less than two plaque forming units per ml was detectable in these preparations, so that the background of endogenous infectivity was exceedingly low. We have now discovered that products of the in vitro replicase reaction according to the invention may be used as the core particles for transcapsidation. Thus, when a transcript of a cloned (and manipulated) rotavirus cDNA is used as one of the exogenous (+)-strand RNAs, together with mRNAs for the other genes, the replicase reaction is capable of producing core particles containing the dsRNA form of the rotavirus cDNA. Then, when this core particle resulting from the replicase reaction is transcapsidated, an infectious particle containing the cloned gene can be obtained. This constitutes a generally applicable system for the rescue of cloned and manipulated genes into infectious rotavirus.

This example demonstrates rescue, by showing rescue of exogenously added B223 mRNA in a replicase system containing open cores derived from SA11-4F. A 100 ul basic replicase reaction was performed that contained 1.6 ug of SA11-4F open cores, 3.6 ug of B223 mRNA, and all four NTPs at a concentration of 1.25 mM. None of the NTPs was radioactive. After a three hour incubation, the reaction was adjusted to high salt by addition of 0.1 volume of 10×salt buffer (500 mM Tris-HCl, pH 7.6; 1000 mM NaCl, 200 mM $CaCl_2$; 100 mM KCl; 50 mM $MgCl_2$) and incubated a further 30 minutes at 37° C. to "re-close" the opened cores.

The resulting replicase products were then subjected to sequential transcapsidation as published, and the entire resulting population of particles was subjected to plaque assay on MA104 cells. If no exogenous mRNA was added to the system, 19 plaques appeared on the plates. Analysis of the genome of these plaques by PAGE revealed that all had an SA11-4F genotype. This is expected, as the basic reaction synthesizes SA11-4F dsRNA on the endogenous RNAs present in the open cores, if no exogenous RNA is added. When exogenous B223 RNA was added to the system, 29 plaques were obtained. Of these, 27 contained the SA11-4F genome and two of the plaques contained the genome segments of B223, indicating that they had come from core particles that had replicated the exogenous mRNA, been transcapsidated, and produced plaques in the assay. Finally, if the open cores were omitted from the initial replicase reaction, no plaques were obtained in the experiment. This confirms that the infectious particles that gave rise to the plaques resulted from in vitro replicase activity to produce potentially infectious cores that were rendered infectious by transcapsidation. This example demonstrates that exogenous viral mRNAs can be rescued to produce infectious virus. One of ordinary skill in the art will recognize that this example will apply equally well to the rescue of transcripts of cloned and manipulated genes using native and bac-cores from any rotavirus strain or other member of the Reoviridae.

What is claimed is:

1. A method for the in vitro replication of a Reoviridae virus RNA comprising:

reacting Reoviridae virus open core particles and Reoviridae virus mRNA in a solution also comprising nucleotide tri-phosphates.

2. A method for the in vitro replication of rotavirus RNA comprising:

reacting rotavirus open core particles and rotavirus mRNA in a solution also comprising nucleotide tri-phosphates.

3. The method according to claim 2 wherein said rotavirus open core particles are derived from naturally occurring rotavirus particles.

4. The method according to claim 2 wherein said rotavirus open core particles are derived from Bac-ss particles produced by co-expression of rotavirus genes coding for VP1, VP2, VP3 and $VP_6$ in a baculovirus expression system.

5. The method according to claim 2 wherein said rotavirus mRNA is obtained from naturally occurring rotavirus.

6. The method according to claim 2 wherein said rotavirus mRNA is transcribed from rotavirus cDNA.

7. The method according to claim 2 wherein said rotavirus mRNA is transcribed from genetically manipulated rotavirus cDNA.

8. A composition of matter comprising:

open core particles of a Reoviridae virus;

mRNA of said Reoviridae virus or related Reoviridae strain thereof;

and nucleotide tri-phosphates.

9. A composition of matter comprising:

rotavirus open core particles;

rotavirus mRNA; and nucleotide tri-phosphates.

10. The composition of matter according to claim 9 wherein said rotavirus open core particles are derived from naturally occurring rotavirus particles.

11. The composition of matter according to claim 9 wherein said rotavirus open core particles are derived from Bac-ss particles produced by co-expression of rotavirus genes coding for VP1, VP2, VP3 and VP6 in a baculovirus expression system.

12. An in vitro replication kit comprising:

rotavirus open-cove particles.

13. The in vitro replication kit of claim 12, further comprising:

Tris-HCl;

Magnesium Acetate;

ribonucleotide tri-phosphates;

dithiothreitol;

RNasin, and polyethylene glycol.

14. A method for the incorporation of exogenous genes into infectious Reoviridae virus comprising:

reacting Reoviridae open core particles and Reoviridae virus mRNA in a solution also comprising nucleotide tri-phosphates thereby producing replicase products, and transcapsidating said replicase products, wherein said mRNA comprises a segment of exogenous Reoviridae virus mRNA.

15. The method according to claim 14 wherein said exogenous Reoviridae virus mRNA comprises a segment of MRNA transcribed from genetically manipulated Reoviridae virus cDNA.

16. The method according to claim 14 wherein said exogenous Reoviridae virus mRNA comprises a segment of mRNA that corresponds to a strain that is different from the strain that corresponds to the open core particles.

17. The method according to claim 14 wherein said open core particles are derived from naturally occurring virus particles.

18. The method according to claim 14 wherein said exogenous Reoviridae virus is obtained from naturally occurring virus.

19. The method according to claim 14 wherein said exogenous Reoviridae virus mRNA is transcribed from Reoviridae virus cDNA.

20. The method according to claim 14 wherein said exogenous Reoviridae virus mRNA is transcribed from genetically manipulated Reoviridae virus cDNA.

21. A method for the incorporation of exogenous genes into infectious rotavirus comprising:

reacting rotavirus open core particles, rotavirus mRNA and a segment of exogenous Reoviridae virus mRNA in a solution also comprising nucleotide tri-phosphates thereby producing replicase products, and transcapsidating said replicase products.

22. The method according to claim 21 wherein said exogenous Reoviridae virus mRNA comprises a segment of mRNA transcribed from genetically manipulated Reoviridae virus cDNA.

23. The method according to claim 21 wherein said rotavirus mRNA comprises a segment of mRNA that corresponds to a rotavirus strain that is different from the rotavirus strain that corresponds to the open core particles.

24. The method according to claim 21 wherein said rotavirus open core particles are derived from naturally occurring rotavirus particles.

25. The method according to claim 21 wherein said rotavirus open core particles are derived from Bac-ss particles produced by co-expression of rotavirus genes coding for VP1, VP2, VP3 and VP6 in a baculovirus expression system.

26. The method according to claim 21 wherein said rotavirus mRNA is obtained from naturally occurring rotavirus.

27. The method according to claim 21 wherein said exogenous mRNA is transcribed from cDNA.

28. The method according to claim 21 wherein said exogenous mRNA is transcribed from genetically manipulated cDNA.

29. A rotavirus open core.

30. A Reoviridae virus open core.

31. A method for making a Reoviridae virus particle comprising:

reacting Reoviridae virus open core particles and Reoviridae virus mRNA in a solution also comprising nucleotide tri-phosphates thereby producing replicase products; and transcapsidating said replicase products thereby producing a Reoviridae virus particle.

32. A method for the making a rotavirus particle comprising:

reacting rotavirus open core particles and rotavirus mRNA in a solution also comprising nucleotide triphosphates thereby producing replicase products; and transcapsidating said replicase products thereby producing a rotavirus particle.

33. A method according to claim 31 wherein said Reoviridae virus particle is infectious.

34. A method according to claim 31 wherein said Reoviridae virus particle is non-naturally occurring.

35. A method according to claim 32 wherein said Rotavirus particle is infectious.

36. A method according to claim 32 wherein said Rotavirus particle is non-naturally occurring.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 54 base pairs
( B ) TYPE: nucleic acid
( C ) STRANDEDNESS: single
( D ) TOPOLOGY: unknown ( i i ) MOLECULE TYPE: cDNA ( x i ) SEQUENCE DESCRIPTION: SEQ ID NO:1:

CCAGGTACCT AATACGACTC ACTATAGGCT TTAAAAGAGA GAATTTCCGA CTGG 54

( 2 ) INFORMATION FOR SEQ ID NO:2:

( i ) SEQUENCE CHARACTERISTICS:
( A ) LENGTH: 35 base pairs
( B ) TYPE: nucleic acid
( C ) STRANDEDNESS: single
( D ) TOPOLOGY: unknown ( i i ) MOLECULE TYPE: cDNA ( x i ) SEQUENCE DESCRIPTION: SEQ ID NO:2:

GGTAAGCTTC CGCGGTCACA TCATACAGTT CTAAC 35